(12) United States Patent
Lin et al.

(10) Patent No.: US 8,689,800 B2
(45) Date of Patent: * Apr. 8, 2014

(54) MAGNETIC NAVIGATION CONTROL APPARATUS

(75) Inventors: Ray-Lee Lin, Tainan (TW); Sheng-Fu Hsiao, Kaohsiung (TW)

(73) Assignees: National Cheng Kung University, Tainan (TW); Delta Electronics, Inc., Taoyuan Hsien (TW)

( * ) Notice: Subject to any disclaimer, the term of this patent is extended or adjusted under 35 U.S.C. 154(b) by 118 days.

This patent is subject to a terminal disclaimer.

(21) Appl. No.: 13/210,014

(22) Filed: Aug. 15, 2011

(65) Prior Publication Data

US 2012/0103348 A1 May 3, 2012

(30) Foreign Application Priority Data

Oct. 29, 2010 (TW) ................................ 99137298 A

(51) Int. Cl.
*A61B 19/00* (2006.01)
*H01F 1/00* (2006.01)

(52) U.S. Cl.
USPC .......................................... 128/899; 335/296

(58) Field of Classification Search
USPC ........... 128/899; 600/424; 335/297; 310/179, 310/186
See application file for complete search history.

(56) References Cited

U.S. PATENT DOCUMENTS

| | | | |
|---|---|---|---|
| 5,986,376 A * | 11/1999 | Werson | 310/186 |
| 2006/0165805 A1 | 7/2006 | Steinhoff et al. | |
| 2007/0299550 A1 | 12/2007 | Nishijima et al. | |
| 2010/0156399 A1 | 6/2010 | Chiba et al. | |

FOREIGN PATENT DOCUMENTS

CN 101795615 A 8/2010

* cited by examiner

*Primary Examiner* — Jacqueline Cheng
*Assistant Examiner* — Kaylee Wilson
(74) *Attorney, Agent, or Firm* — Muncy, Geissler, Olds & Lowe, P.C.

(57) ABSTRACT

A magnetic navigation control apparatus includes a sensing unit, a control unit and a magnetic field generating unit. The sensing unit generates a sensing signal according to the position of a magnetic element. The control unit is electrically connected with the sensing unit and generates a first control signal and a second control signal according to the sensing signal. The magnetic field generating unit is electrically connected with the control unit and has a housing, a plurality of interpoles, and a plurality of short poles. The interpoles are disposed in the housing. The short poles are disposed between the interpoles evenly. The magnetic field generating unit generates a navigation signal according to the first control signal, thereby controlling the magnetic element to move in at least one direction within a target region. The magnetic navigation control apparatus has greater magnetic navigation effects, and can thus reduce the cost.

17 Claims, 10 Drawing Sheets

MAGNETIC NAVIGATION CONTROL APPARATUS

CROSS REFERENCE TO RELATED APPLICATIONS

This Non-provisional application claims priority under 35 U.S.C. §119(a) on Patent Application No(s). 099137298 filed in Taiwan, Republic of China on Oct. 29, 2010, the entire contents of which are hereby incorporated by reference.

BACKGROUND OF THE INVENTION

1. Field of Invention

The invention relates to a navigation control apparatus and, in particularly, to a magnetic navigation control apparatus.

2. Related Art

The process of targeted therapy is that injects targeted drug into a body to attack specific cells and thus achieve the treating effect. However, the targeted drug injection disperses in the body to reduce the effect of the targeted therapy. In addition, the dispersion of the drug causes the significant side effect, and another injury, to the patient.

In order to improve the effect of the targeted therapy, a magnetic navigation control system combined with the targeted therapy is developed. For effective certain disease treatment, the magnetic field generating device in the magnetic navigation control apparatus is used to generate the magnetic force for guiding magnetic targeted drug to a specific region. The targeted drug can be navigated to the target region according to the magnetic force generated by the magnetic field generating unit. Thus, in addition to the treatment in the specific region, the side effect on the patient is decreased, and thus the treating effect can be enhanced.

A conventional magnetic navigation control apparatus utilizes a magnetic field generating unit 1, as shown in FIGS. 1A and 1B. FIG. 1A shows a cross-sectional view of the conventional magnetic field generating unit 1. FIG. 1B shows a schematic illustration of a magnetic-line distribution for the magnetic field generating unit 1 in FIG. 1A.

The magnetic field generating unit 1 includes a housing 11, three poles 121 to 123 and a plurality of windings 13. The housing 11 has an inner side 111. The poles 121 to 123 are disposed on the inner side 111 in the housing 11 with the included angle between the poles 121 to 123 at the center point being equal to 120 degrees. In addition, the windings 13 are disposed corresponding to the poles 121 to 123, respectively. Powering the windings 13 alternately can make the magnetic field generating unit 1 generate the magnetic lines, as shown in FIG. 1B, in which the winding 13 corresponding to the pole 121 is powered.

However, the magnetic-line distribution for the magnetic field generating unit 1 is relatively nonuniform and less concentrated. In addition, due to the magnetoresistive effect of the air, the magnetic flux density and the magnetic force of the magnetic field generating unit 1 are attenuated with the increment of the distance to the pole. Accordingly, the magnetic navigation effect of the magnetic navigation control apparatus is reduced. In order to enhance the magnetic navigation effect, the power for the winding 13 of the magnetic field generating unit 1 has to be increased to prompt the magnetic force for better magnetic navigation effect. However, this can increase the cost.

Therefore, it is an important subject for the invention to provide a magnetic navigation control apparatus that can provide better magnetic navigation effect and reduce the cost.

SUMMARY OF THE INVENTION

In view of the foregoing, the magnetic navigation control apparatus provides better magnetic navigation effect and reduces the cost, which is an important objective.

To achieve the above objective, the invention discloses a magnetic navigation control apparatus for navigating at least one magnetic element to target region. The magnetic navigation control apparatus includes a sensing unit, a control unit, and a magnetic field generating unit. The sensing unit generates a sensing signal according to a position of the magnetic element. The control unit is electrically connected with the sensing unit and generates a first control signal and a second control signal according to the sensing signal. The magnetic field generating unit is electrically connected with the control unit and includes a housing, a plurality of interpoles, and a plurality of short poles. The interpoles are disposed in the housing, and the short poles are disposed between the interpoles evenly. The magnetic field generating unit generates a navigation signal according to the first control signal for controlling the magnetic element to move in at least one direction within the target region.

In one embodiment of the invention, the magnetic element includes a magnetic particle, a magnetic drug, a medical catheter, a medical machine, or their combinations.

In one embodiment of the invention, the navigation signal is a magnetic signal for moving the magnetic element by attraction or repulsion.

In one embodiment of the invention, the housing includes an annular section and an inner side. The interpoles of the magnetic field generating unit are disposed on the inner side in the housing and have the same intervals arranged around an inner periphery of the annular section.

In one embodiment of the invention, when the number of the interpoles is equal to three, an included angle between the interpoles at a center point of the annular section in the housing is equal to 120 degrees.

In one embodiment of the invention, a first interval is formed between the adjacent short poles, and a second interval equal to the first interval is formed between the interpoles and the short poles adjacent to the interpole.

In one embodiment of the invention, an included angle between the adjacent short poles at a center point of the annular section in the housing is equal to 5, 10, 12 or 15 degrees.

In one embodiment of the invention, the number of the interpoles for the magnetic field generating unit is three or more.

In one embodiment of the invention, the number of the short poles for the magnetic field generating unit is equal to 69, 33, 27 or 21.

In one embodiment of the invention, the magnetic field generating unit further includes a plurality of windings respectively disposed corresponding to the interpoles. Each of the windings has a plurality of coils located between the interpoles and the short poles.

In one embodiment of the invention, the apparatus further includes a moving unit electrically connected with the control unit for moving the magnetic element relative to the moving unit in an additional direction to the target region according to the second control signal.

In one embodiment of the invention, the moving unit includes a patient table and a driver. The driver drives the patient table to move in the additional direction according to the second control signal, so that the magnetic element can be moved relative to the moving unit to the target region.

In one embodiment of the invention, the first control signal includes a direct current signal or a pulse signal.

In one embodiment of the invention, the first control signal includes an overdrive current signal.

In one embodiment of the invention, the overdrive current signal and the first control signal are in phase or out of phase.

As mentioned above, the magnetic navigation control apparatus of the invention includes a magnetic field generating unit for generating a navigation signal according to the first control signal. Referring to the navigation signal, the magnetic element is controlled to move in at least one direction within the target region. The interpoles of the magnetic field generating unit are disposed in the housing, and the short poles thereof are evenly disposed between the interpoles, the first interval is formed between the adjacent short poles. Based on the design for the magnetic field generating unit in the invention, the magnetic field generating unit has more concentrated and more uniform magnetic-line distribution than the conventional ones. So that the magnetic navigation control apparatus in the invention has better magnetic navigation effect. Moreover, since the magnetic field generating unit of the invention can effectively promote the magnetic flux density and the magnetic force in the working region, the conversion efficiency of the magnetic navigation control apparatus can be enhanced, thereby further decreasing the cost. In addition, in one embodiment of the invention, the moving unit is configured to move the magnetic element relative to the moving unit in an additional direction to the target region according to the second control signal. Thus, the magnetic element can be navigated to the target region. Regarding to the medical application, the magnetic navigation control apparatus of the invention can further enhance the therapy effect, decrease the side effect on the patient, and sufficiently reduce the medical cost.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 2A:
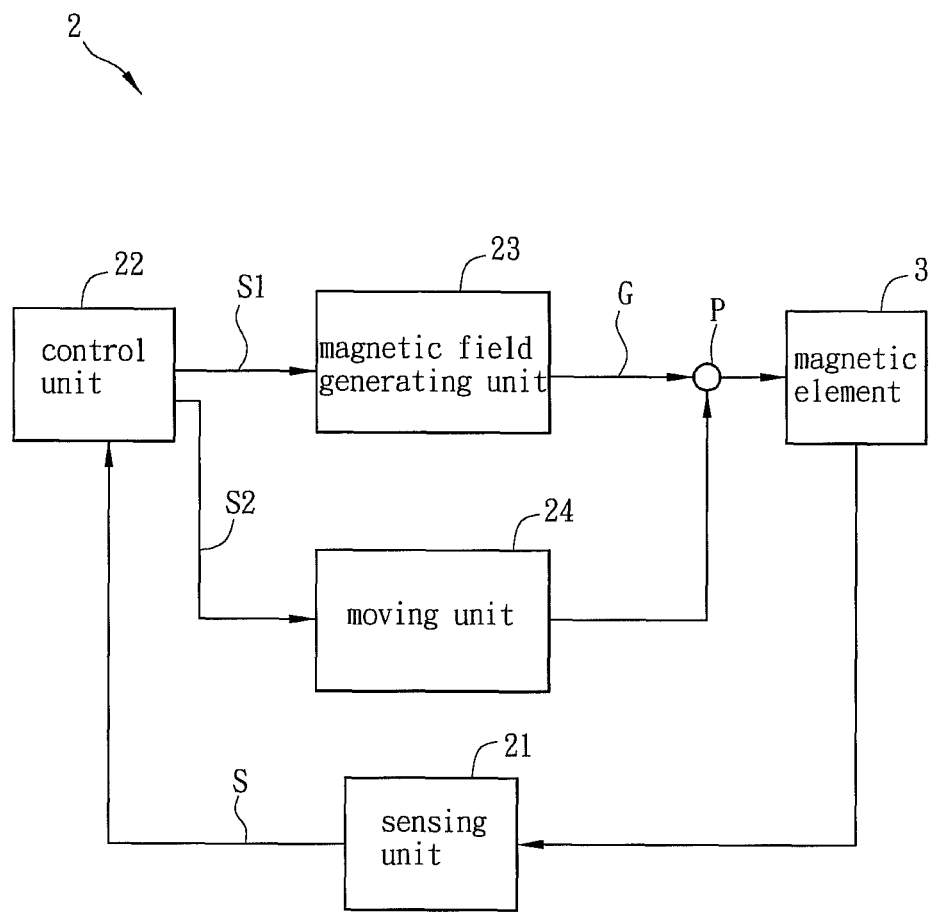
FIG. 2A shows a functional block diagram of a magnetic navigation control apparatus for the invention.
Figure 2B:
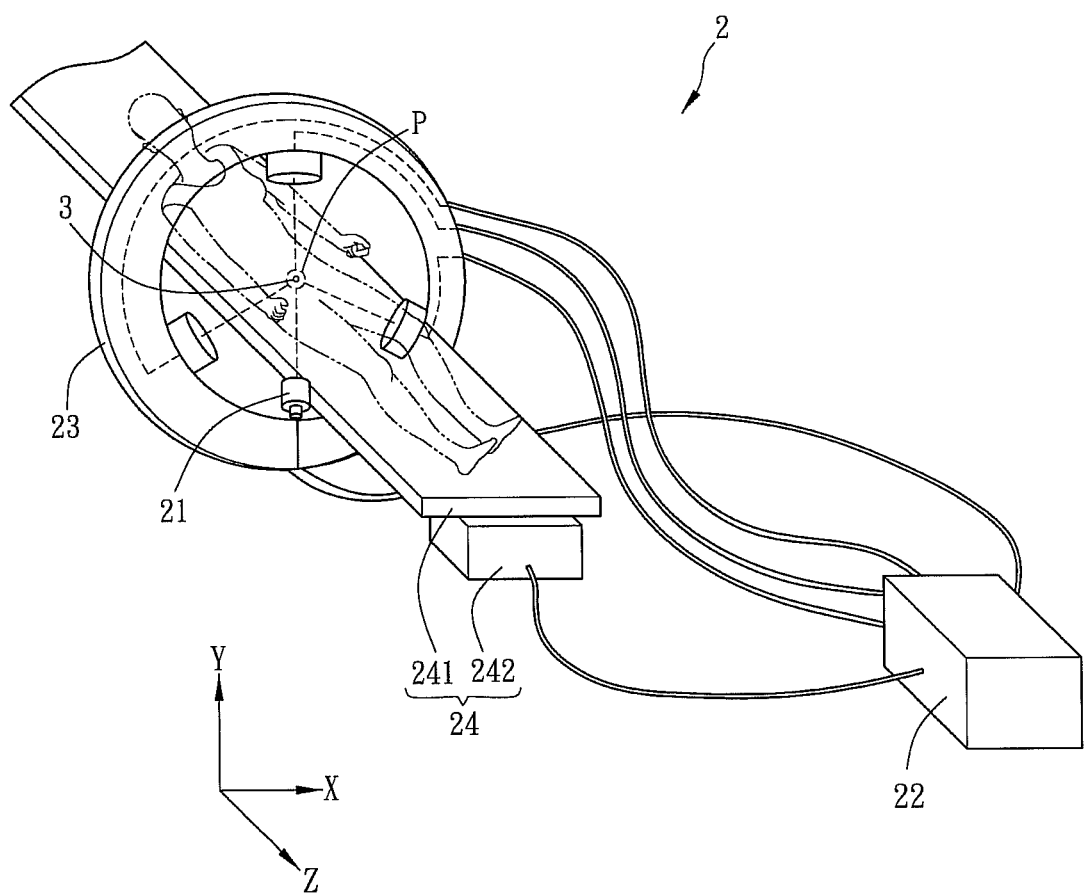
FIG. 2B shows a schematic illustration of the magnetic navigation control apparatus.

FIG. 2A shows a functional block diagram of a magnetic navigation control apparatus 2 in the invention. FIG. 2B shows a schematic illustration of the magnetic navigation control apparatus 2. Referring to FIGS. 2A and 2B, the magnetic navigation control apparatus 2 is used for navigating at least one magnetic element 3 in a target region P. The magnetic navigation control apparatus 2 is applied to the medical applications of targeted therapy, cardiovascular therapeutics, medical micro-machine navigation, surgical catheter orientation navigation and the likes. Of course, the magnetic navigation control apparatus 2 is applied to the non-medical applications.

In this embodiment, the magnetic navigation control apparatus 2 includes a sensing unit 21, a control unit 22, a magnetic field generating unit 23 and a moving unit 24.

The sensing unit 21 generates a sensing signal S according to the position of the magnetic element 3. In other words, the sensing unit 21 can detect the position of the magnetic element 3, and then generate the sensing signal S. In this embodiment, the magnetic element 3 may include, for example but not limited to, a magnetic particle, a magnetic drug, a medical catheter, a medical machine (micro-machine), or any of their combinations. The magnetic particle is, for example but not limited to, the nano-magnetic particle, nano-magnetic drug, and the likes.

The control unit 22 is electrically connected with the sensing unit 21. The control unit 22 generates a first control signal 51 and a second control signal S2 according to the sensing signal S. In this embodiment, the control unit 22 receives the sensing signal S generated by the sensing unit 21, and then outputs the first control signal S1 and the second control signal S2 accordingly.

The magnetic field generating unit 23 is electrically connected with the control unit 22. The magnetic field generating unit 23 generates a navigation signal G according to the first control signal S1. The navigation signal G can control the magnetic element 3 to move in at least one direction within the target region P by attraction or repulsion. In this embodiment, the first control signal S1 is a current signal for driving the magnetic field generating unit 23 to generate the navigation signal G. The navigation signal G is substantially a magnetic force signal, which can navigate and control the magnetic element 3 to move in the direction of the X and/or Y axis within the target region P (see FIG. 2B). Accordingly, the magnetic element 3 can be moved in the X and/or Y axis within the target region P. Herein, the target region P locates in a working region inside the magnetic field generating unit 23, and the working region locates in a human body.

Figure 3A:
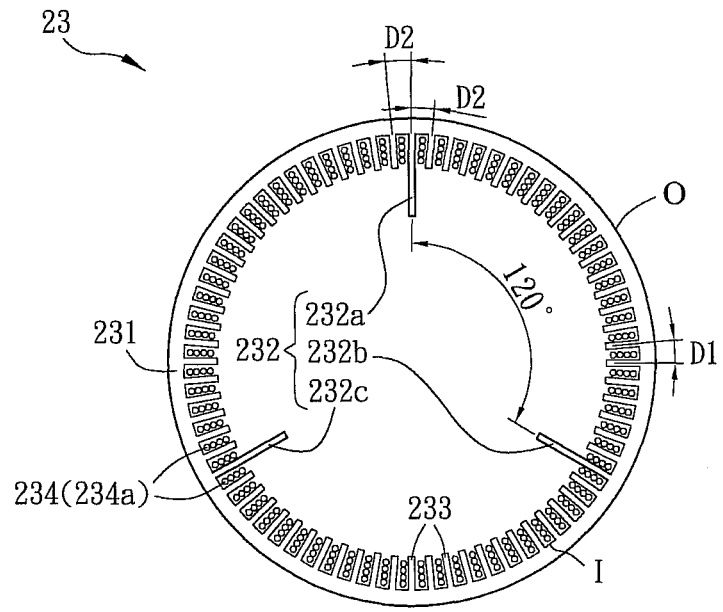
FIG. 3A shows a cross-sectional view of a magnetic field generating unit in the invention.

In addition, the detailed structure of the magnetic field generating unit 23 is described hereinafter with reference to FIG. 3A, which shows a cross-sectional view of the magnetic field generating unit 23.

The magnetic field generating unit 23 includes a housing 231, a plurality of interpoles 232, and a plurality of short poles 233. Herein, the housing 231 is a substantially hollow cylinder, wherein the housing 231 has an annular section, an inner side I and an outer side O. In addition, the materials of the housing 231, the interpoles 232 and the short poles 233 include magnetic material or superconductor, such as the silicon steel, amorphous alloy, ferromagnetic, ferrite or the like. In addition, the housing 231 and at least one of the interpoles 232 or the short poles 233 are integrally formed. In this illustrative embodiment, the housing 231, the interpoles 232 and the short poles 233 are integrally formed.

The interpoles 232 are disposed on the inner side I in the housing 231 and have the same intervals arranged around the inner periphery of the annular section in the housing 231. In this embodiment, three interpoles 232 are provided. Herein, the three interpoles 232 are referred to as specific interpoles 232a to 232c evenly disposed on the inner side I. In other words, three specific interpoles 232a to 232c of this embodiment are evenly located on the inner side I of the housing 231. So that included angles between any two specific interpoles (i.e., between the specific interpoles 232a and 232b, between the specific interpoles 232b and 232c and between the specific interpoles 232c and 232a) at the center point of the annular section in the housing 231 are equal to 120 degrees, as shown in FIG. 2A. Nevertheless, the designer disposes six or more than six specific interpoles on the inner side I according to the requirement for the magnetic force and evenly arranges the specific interpoles around the inner periphery of the annular section in the housing 231.

The short poles 233 are evenly distributed between the interpoles 232 so that the magnetic field generating unit 23 has a magnetic interpole structure. In this embodiment, the number of short poles 233 is equal to 69. Since the number of interpoles 232 is equal to 3, every 23 short poles 233 are evenly located between two interpoles 232. In addition, a first interval D1 is formed between two adjacent short poles 233. A second interval D2 equal to the first interval D1 is formed between each interpole 232 and adjacent short pole 233. Herein, the sum of the numbers of the specific interpoles 232a to 232c and the short poles 233 is equal to 72. The first interval D1 is equal to the second interval D2, so the included angle between two adjacent short poles 233 at the center point of the annular section in the housing 231 is equal to 5 degrees (360 degrees divided by 72). The included angle between each interpole 232 and adjacent short pole 233 at the center point of the annular section in the housing 231 is also equal to 5 degrees.

The different numbers of short poles 233 are specified according to the requirement on the magnetic force. For example, three specific interpoles 232a to 232c can work in conjunction with 33, 27 or 21 short poles 233. So that the included angle between two adjacent short poles 233 at the center point of the annular section of the housing 231 is equal to 10 (360 divided by 36), 12 (360 divided by 30) or 15 (360 divided by 24) degrees. Herein, the sum of the numbers of the interpoles 232 and the short poles 233 is not particularly restricted.

The length ratio of the short pole 233 to the interpole 232 is adjustable. The designer also adjusts the length ratio according to the requirement on the magnetic force. For example, the length ratio of the short pole 233 to the interpole 232 may be 0.4:1, 0.7:1 or any other ratio.

In addition, the magnetic field generating unit 23 may further include a plurality of windings 234, which are respectively disposed corresponding to the interpoles 232, and located between the interpoles 232 and the short poles 233. In this embodiment, each winding 234 has a plurality of coils 234a disposed respectively corresponding to the specific interpoles 232a to 232c, and respectively located between each of the specific interpoles 232a to 232c and the short poles 233. The material of the coil 234a includes, for example but not limited to, copper, superconductor or any other electroconductive material.

Figure 3B:
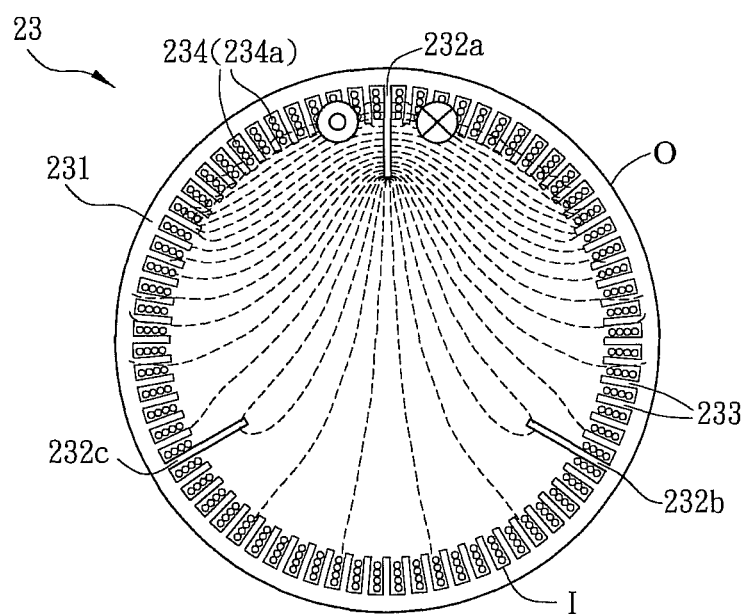
FIG. 3B shows a schematic illustration of a magnetic-line distribution for the magnetic field generating unit in FIG. 3A.

When the control unit 22 outputs the first control signal S1 to power on the winding 234 of the magnetic field generating unit 23, the magnetic-line distribution for the magnetic field generating unit 23 is shown in FIG. 3B, for example, wherein FIG. 3B shows the distribution when the winding 234 corresponding to the specific interpole 232a is powered on. Because the magnetic interpole structure is used in the magnetic field generating unit 23, the provision of the short pole 233 can decrease the magnetoresistive effect of the air between two interpoles 232, and enhance the magnetic force attenuation of the magnetic field generating unit 23. So that the magnetic lines generated by the winding 234 corresponding to the interpole 232 can be effectively extended. Thus, the magnetic-line distribution of the magnetic field generating unit 23 becomes more concentrated and more uniform.

Figure 1A:
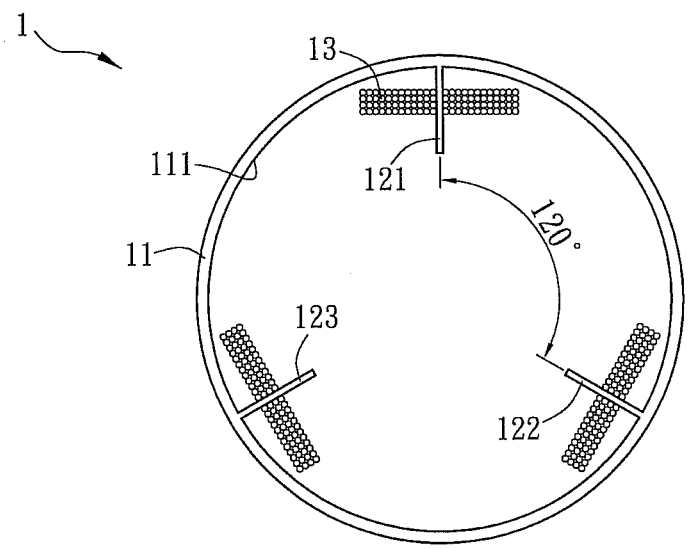
FIG. 1A shows a cross-sectional view of a conventional magnetic field generating unit.
Figure 1B:
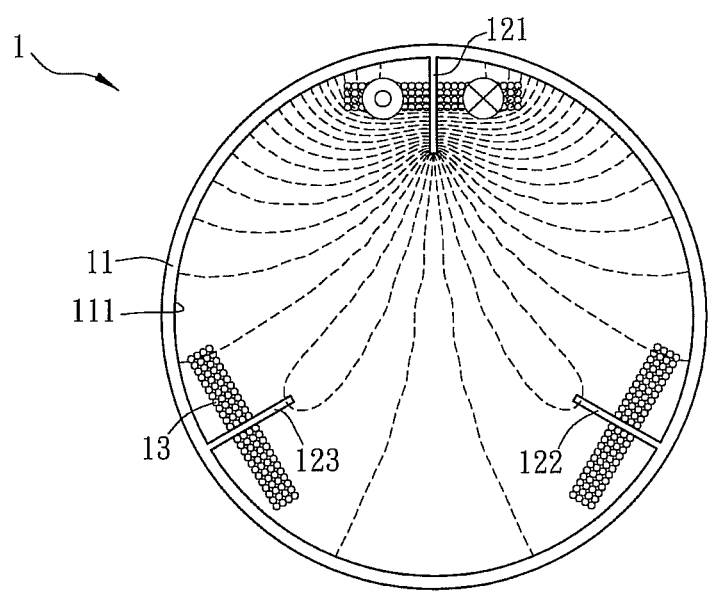
FIG. 1B shows a schematic illustration of a magnetic-line distribution of the magnetic field generating unit of FIG. 1A.

Comparing the magnetic-line distribution in FIG. 3B with that in FIG. 1B, the result is found that the magnetic field generating unit 23 in FIG. 3B has the more uniformly distributed and more concentrated magnetic lines than the magnetic field generating unit 1 in FIG. 1B.

Figure 4A:
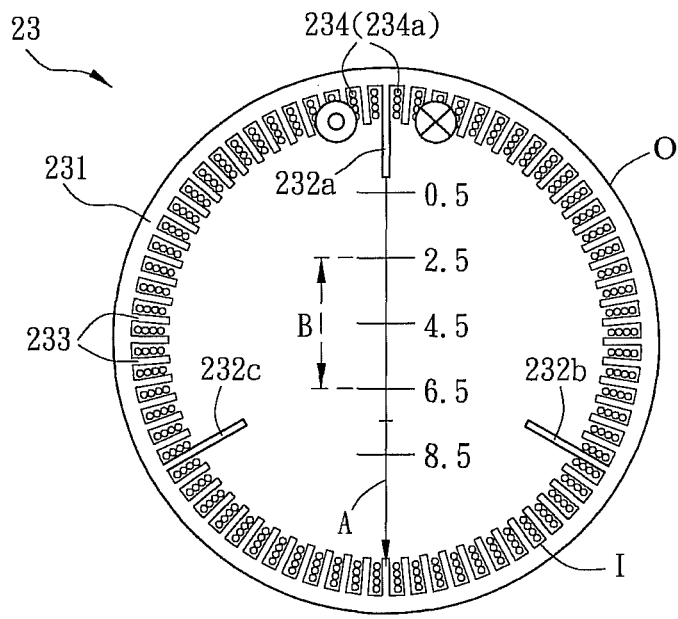
FIG. 4A shows a cross-sectional view of the magnetic field generating unit in the invention.
Figure 4B:
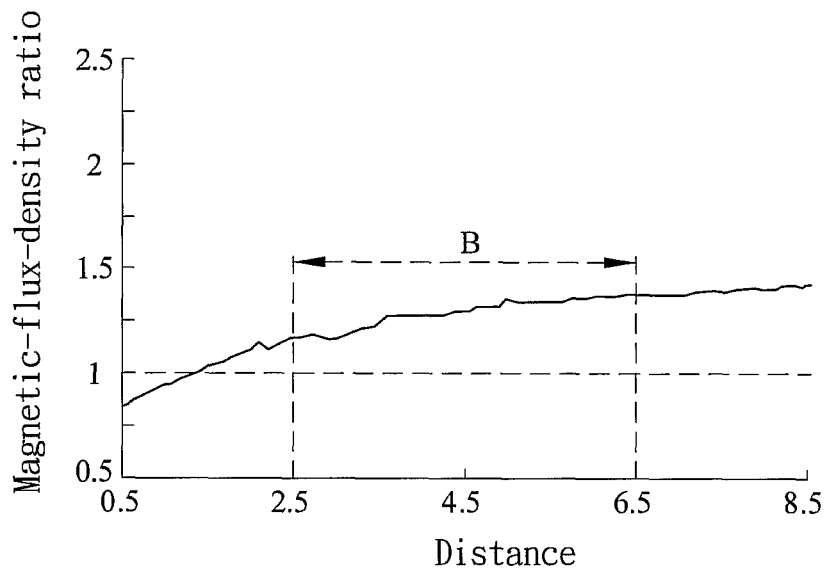
FIG. 4B shows a schematic graph of the comparison between the magnetic flux densities for the magnetic field generating unit in the invention and the conventional magnetic field generating unit.

In addition, please refer to FIGS. 4A and 4B. FIG. 4B shows a schematic illustration of the comparison between the magnetic flux densities for the magnetic field generating unit 23 in the invention and the conventional magnetic field generating unit 1. The horizontal coordinate in FIG. 4B represents the distance between a certain position on the straight line A of FIG. 4A and the top end of the specific interpole 232a, while the vertical coordinate of FIG. 4B represents the ratio of the magnetic flux density for the magnetic field generating unit 23 in the invention to the magnetic flux density for the conventional magnetic field generating unit 1.

As shown in FIG. 4B, the ratio of the magnetic flux densities becomes higher as the distance from the top end of the specific interpole 232a gets longer. In other words, as the distance from the specific interpole 232a gets longer, the improvement on the magnetic flux density for the magnetic field generating unit 23 becomes greater than that of the conventional one. In addition, in a working region B (may include the target region P) with the distance ranging from 2.5 to 6.5 units, the magnetic flux density of the magnetic field generating unit 23 is equal to 1.2 to 1.4 times of that for the magnetic field generating unit 1. In addition, the magnetic field generating unit 23 has the symmetrical structure. So, in the same condition, the magnetic flux densities corresponding to the specific interpoles 232b and 232c comparing with the prior art is similarly enhanced.

Figure 5A:
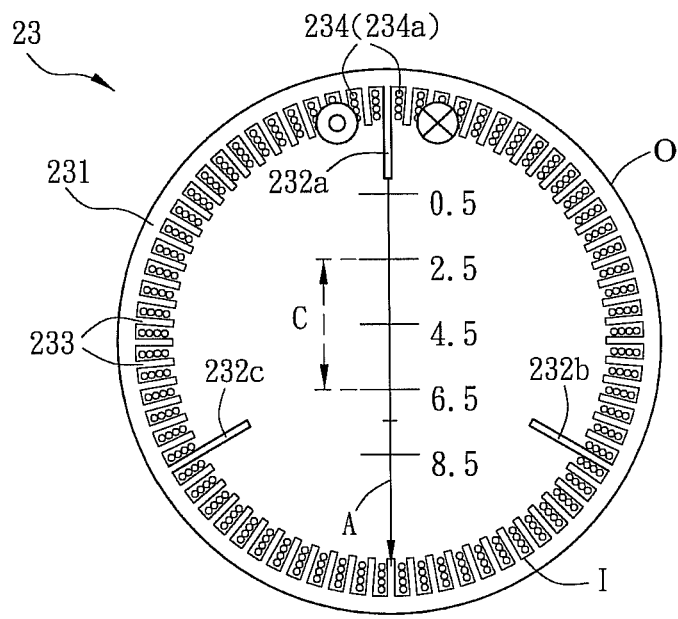
FIG. 5A shows a cross-sectional view of the magnetic field generating unit in the invention.
Figure 5B:
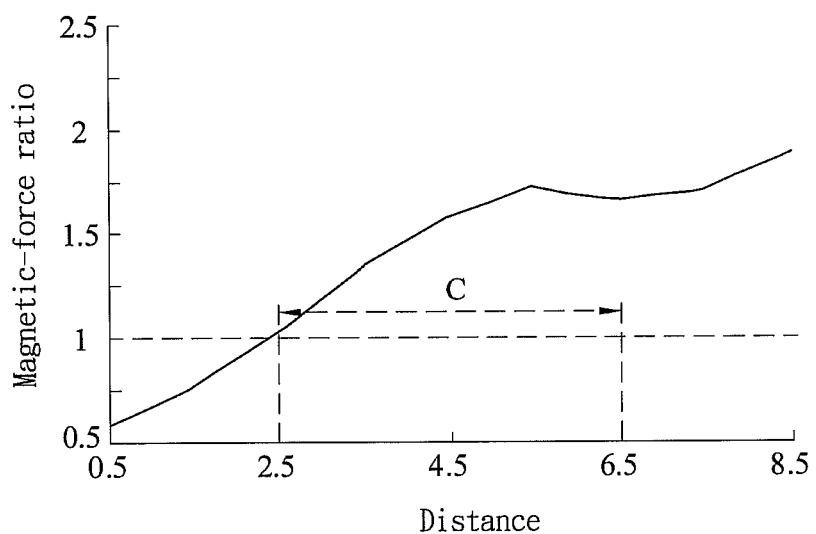
FIG. 5B shows a schematic graph of the comparison between the magnetic forces for the magnetic field generating unit in the invention and the conventional magnetic field generating unit.

Furthermore, please refer to FIGS. 5A and 5B. FIG. 5B shows a schematic illustration of the comparison between the magnetic forces for the magnetic field generating unit 23 in the invention and the magnetic field generating unit 1. The horizontal coordinate in FIG. 5B represents the distance between a certain position on the straight line A of FIG. 5A and the top end of the specific interpole 232a, while the vertical coordinate in FIG. 5B represents the ratio of the magnetic force for the magnetic field generating unit 23 in the invention to the magnetic force for the magnetic field generating unit 1.

As shown in FIG. 5B, in a working region C with the distance ranging from 2.5 to 6.5 units, the magnetic force for the magnetic field generating unit 23 is equal to 1.0 to 1.6 times of the magnetic force for the magnetic field generating unit 1. In addition, the magnetic field generating unit 23 has the symmetrical structure. So, in the same condition, the magnetic flux densities corresponding to the specific interpoles 232b and 232c comparing with the prior art is similarly enhanced.

Figure 6A:
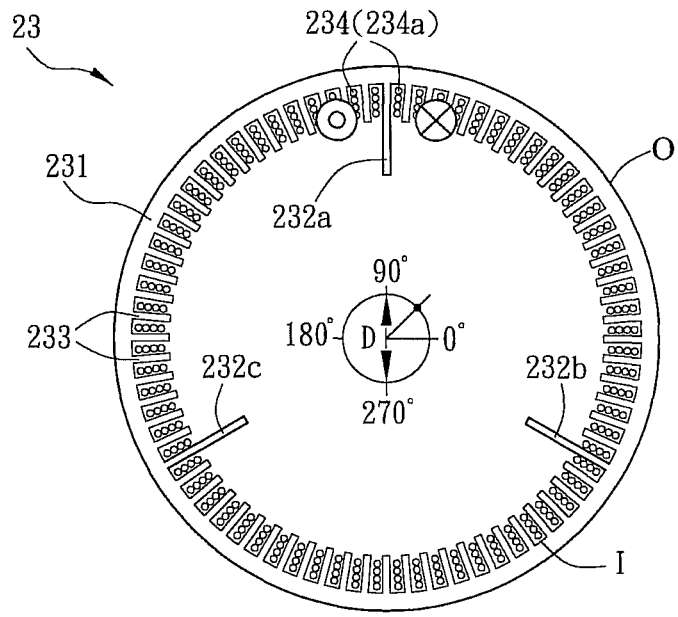
FIG. 6A shows a cross-sectional view of the magnetic field generating unit in the invention.
Figure 6B:
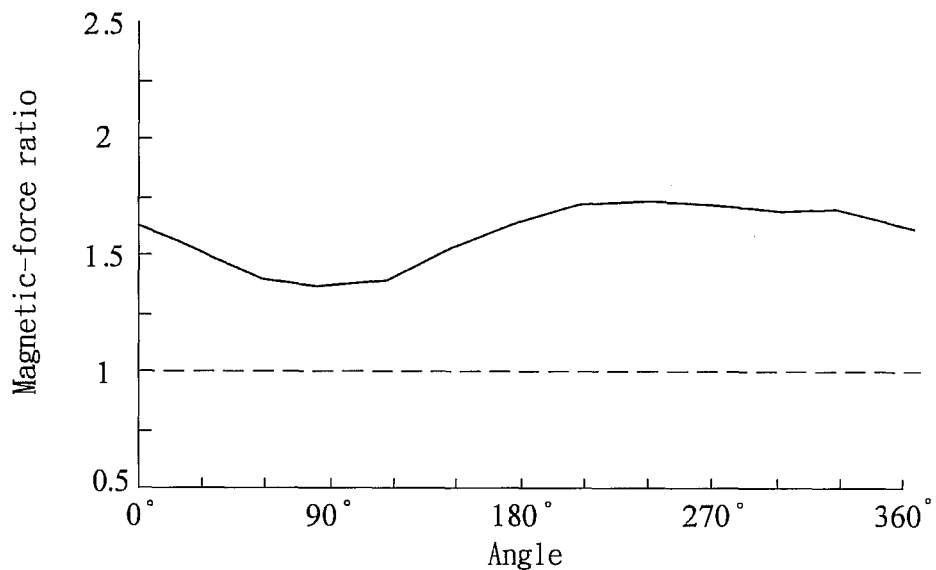
FIG. 6B shows a schematic graph of the comparison between the magnetic forces for the magnetic field generating unit in the invention and the prior art at different azimuths on a circumference of a circle D with a radius equal to 2 units.

Please refer to FIGS. 6A and 6B. FIG. 6B shows a schematic illustration of the comparison between the magnetic forces for the magnetic field generating unit 23 in the invention and the conventional magnetic field generating unit 1 at different azimuths on a circumference of a circle D with a radius equal to 2 units. The horizontal coordinate of FIG. 6B represents the angle on the circumference of the circle D of FIG. 6A, while the vertical coordinate of FIG. 6B represents the ratio of the magnetic force for the magnetic field generating unit 23 in the invention to the magnetic force of the conventional magnetic field generating unit 1.

As shown in FIG. 6B, the magnetic force for the magnetic field generating unit 23 at each of different angles on the circumference of the circle D is equal to 1.4 to 1.7 times of that for the magnetic field generating unit 1. In addition, the magnetic field generating unit 23 has the symmetrical structure. So, in the same condition, the magnetic flux densities corresponding to the specific interpoles 232b and 232c comparing with the prior art is similarly enhanced.

Figure 7A:
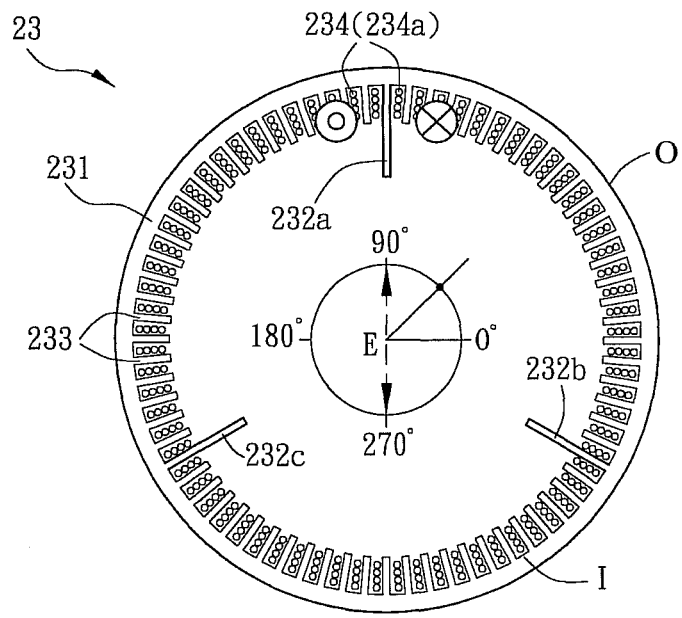
FIG. 7A shows a cross-sectional view of the magnetic field generating unit in the invention.
Figure 7B:
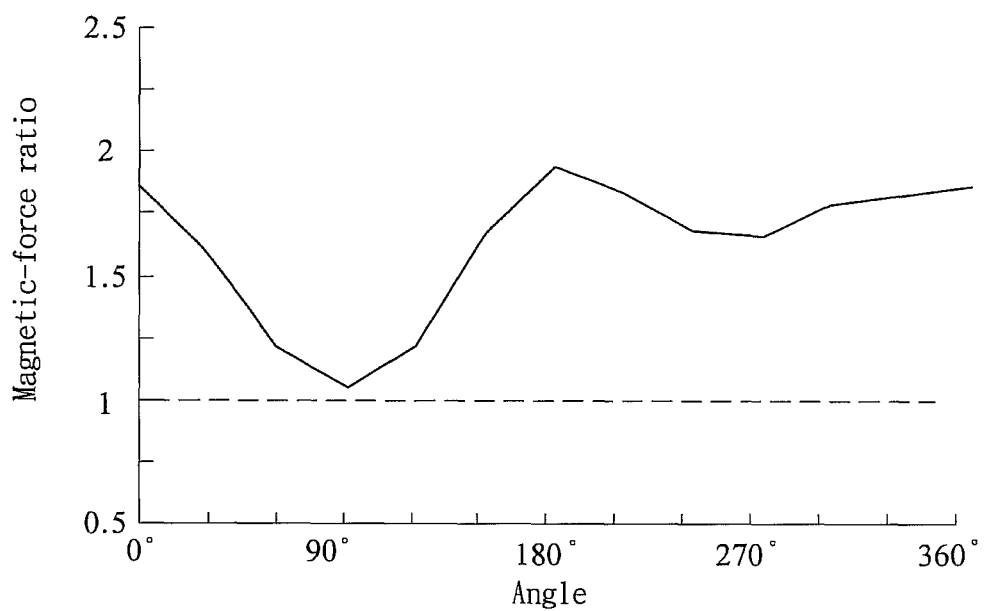
FIG. 7B shows a schematic graph of the comparison between the magnetic forces for the magnetic field generating unit in the invention and the prior art at different azimuths on a circumference of a circle D with a radius equal to 4 units.

Please refer to FIGS. 7A and 7B. FIG. 7B shows a schematic illustration of the comparison between the magnetic forces for the magnetic field generating unit 2 of the invention and the conventional magnetic field generating unit 1 at different azimuths on a circumference of a circle E with a radius equal to 4 units. The horizontal coordinate in FIG. 7B represents the angle on the circumference of the circle E of FIG. 7A, while the vertical coordinate in FIG. 7B represents the ratio of the magnetic force for the magnetic field generating unit 23 in the invention to the magnetic force of the conventional magnetic field generating unit 1.

As shown in FIG. 7B, the magnetic force for the magnetic field generating unit 23 at each of different angles on the circumference of the circle E is equal to 1.0 to 1.9 times of that for the magnetic field generating unit 1. In addition, the magnetic field generating unit 23 has the symmetrical structure. So, in the same condition, the magnetic flux densities corresponding to the specific interpoles 232b and 232c comparing with the prior art is similarly enhanced.

As mentioned above, the design for the short pole 233 of the magnetic field generating unit 23 can decrease the magnetoresistive effect of the air between two interpoles 232 and improve the magnetic force attenuation for the magnetic field generating unit 23. Thus, the magnetic lines generated by the winding 234 corresponding to the interpole 232 can be effectively extended, so that the magnetic-line distribution becomes more concentrated and more uniform. Consequently, the magnetic field generating unit 23 in the invention has capability to generate the more concentrated and more uniform magnetic-line distribution, and can effectively enhance the magnetic flux density and the magnetic force in the working region.

With reference to FIGS. 2A and 2B, the moving unit 24 is electrically connected with the control unit 22, and can move the magnetic element 3 relative to the moving unit 24 in an additional direction to the target region P according to the second control signal S2. In this case, the second control signal S2 includes a voltage or a current signal. In this embodiment, the moving unit 24 includes a patient table 241 and a driver 242. The driver 242, such as a motor or a driving circuit, drives the patient table 241 to move in the Z axis according to the second control signal S2. So that the magnetic element 3 can be moved relative to the moving unit 24 along the Z axis to the target region P.

Figure 8A:
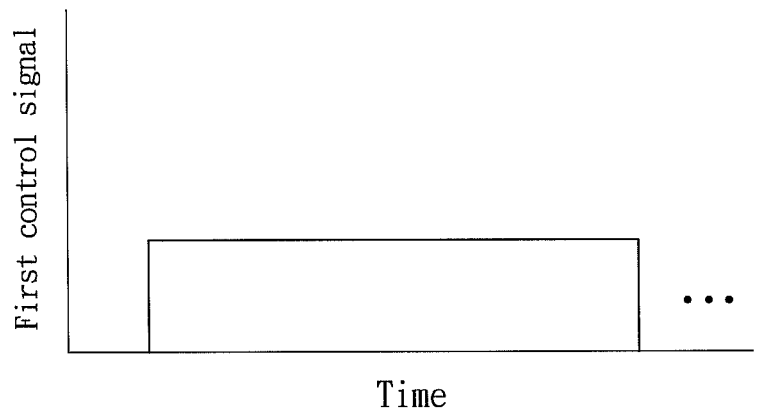
FIGS. 8A to 8D show the waveforms of the first control signals for different aspects.
Figure 8B:
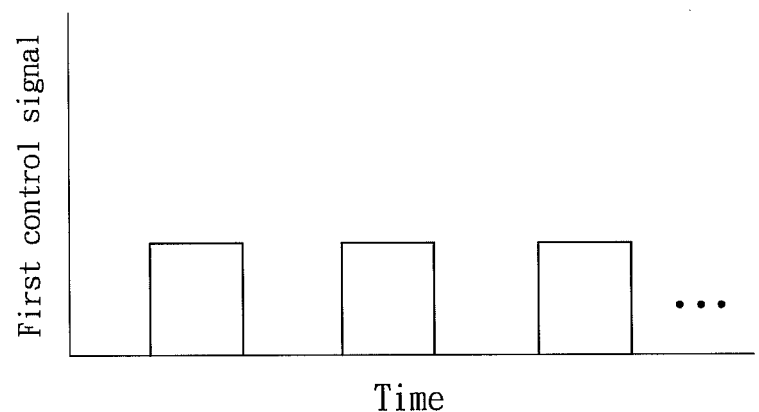

The first control signal S1 may include a direct current signal or a pulse signal. In other words, the control unit 22 outputs the first control signal S1, which is a direct current signal (see FIG. 8A) or include a plurality of pulse signals (see FIG. 8B), for controlling the magnetic field generating unit 23 to generate the required magnetic force.

Figure 8C:
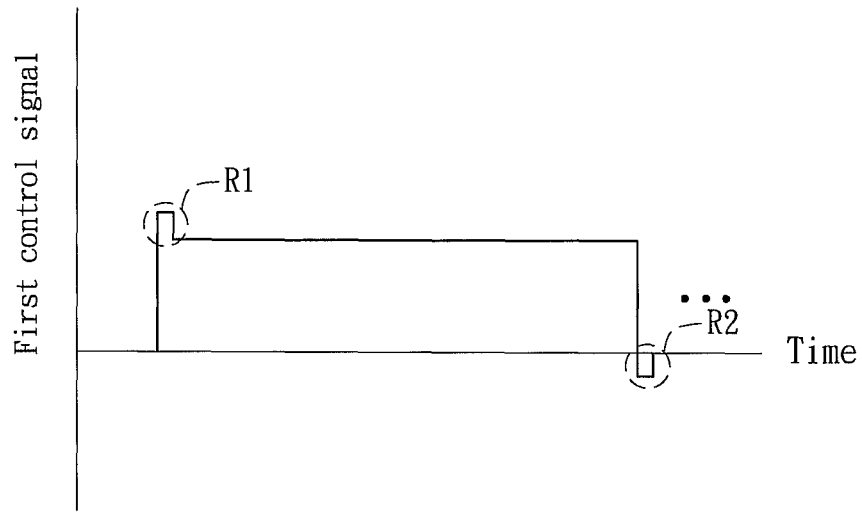
Figure 8D:
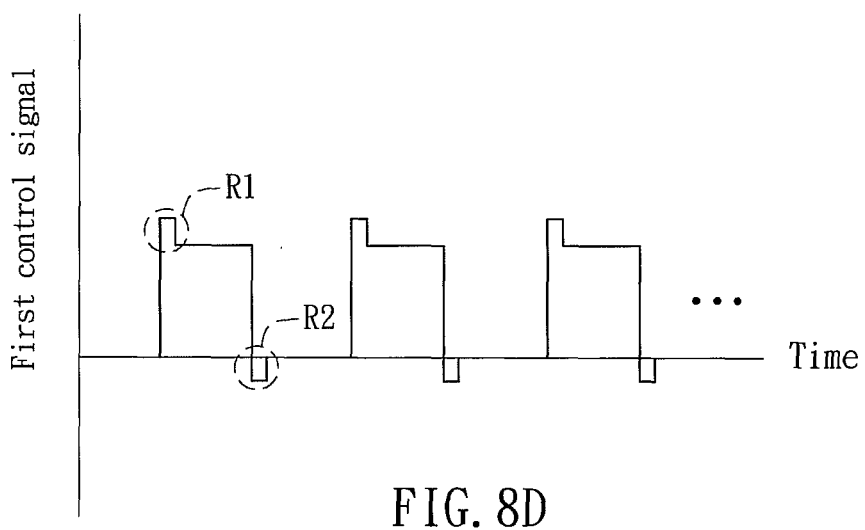

In addition, the first control signal S1 includes an overdrive current signal, and the overdrive current signal and the first control signal S1 are in phase or out of phase. Referring to the region R1 of the waveform shown in FIG. 8C or 8D, the overdrive current signal of the region R1 and the first control signal S1 are in phase. In this case, the magnetic field generating unit 23 generates stronger magnetic force during the starting region, so that the magnetic element 3 easily overcomes the static friction force. In addition, since the magnetic field generating unit 23 has the hysteresis phenomenon, the overdrive current signal with out of phase can also be used to speed the magnetic release of the magnetic field generating unit 23, so that the magnetic element 3 can be immediately stopped. The waveform of the overdrive current signal with out of phase shows as the region R2 of FIG. 8C or 8D. Alternatively, the magnetic field generating unit 23 is also possible to provide a first control signal S1 that includes both an in phase overdrive current signal and an out of phase overdrive current signal. An overdrive current signal is a signal that increases the pulse or direct current signal for a short period of time to make a positive signal, or decreases the pulse or direct current signal lot a period of time to make a negative signal. The term "in phase" means that increasing the pulse or direct current signal for a short period of time to make a positive signal. The term "out of phase" means that decreasing the pulse or direct current signal for a period of time to make a negative signal.

As mentioned above, the magnetic field generating unit 23 of the invention generates the navigation signal G according to the first control signal S1. The navigation signal G can control the magnetic element 3 to move in at least one direction within the target region P. Besides, the moving unit 24 moves in an additional direction according to the second control signal S2, so that the magnetic element 3 can be moved relative to the moving unit 24 in the additional direction to the target region P. Accordingly, the magnetic navigation control apparatus 2 utilizes the sensing unit 21 to detect the position of the magnetic element 3. The magnetic field generating unit 23 and the moving unit 24 is used to navigate the magnetic element 3 to the target region P. In addition, the magnetic field generating unit 23 in the invention generates more concentrated and more uniform magnetic-line distribution than the conventional ones, so that the magnetic navigation control apparatus 2 in the invention has better magnetic navigation effect. Besides, since the greater magnetic force and navigation effect can be obtained without increasing the power for the windings, the conversion efficiency of the magnetic navigation control apparatus can be enhanced, thereby further decreasing the cost.

To sum up, the magnetic navigation control apparatus in the invention includes a magnetic field generating unit for generating a navigation signal according to the first control signal so as to control the magnetic element to move in, at least one direction within the target region. The interpoles of the magnetic field generating unit are disposed in the housing, and the short poles thereof are evenly disposed between the interpoles, the first interval is formed between the adjacent short poles. Based on the design for the magnetic field generating unit in the invention, the magnetic field generating unit has more concentrated and more uniform magnetic-line distribution than the conventional ones. So that the magnetic navigation control apparatus in the invention has better magnetic navigation effect. Moreover, since the magnetic field generating unit in the invention can effectively promote the magnetic flux density and the magnetic force within the working region, the conversion efficiency of the magnetic navigation control apparatus can be enhanced, thereby further decreasing the cost. In addition, in one embodiment of the invention, the moving unit is configured to move the magnetic element relative to the moving unit in an additional direction to the target region according to the second control signal. Thus, the magnetic element can be navigated to the target region. Regarding to the medical application, the magnetic navigation control apparatus in the invention can further improve the therapy effect, decrease the side effect on the patient, and sufficiently reduce the medical cost.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A magnetic navigation control apparatus for navigating at least one magnetic element to a predestined region, comprising:
   a sensing unit generating a sensing signal according to a position of the magnetic element;
   a control unit electrically connected with the sensing unit and generating a first control signal and a second control signal according to the sensing signal; and
   a magnetic field generating unit electrically connected with the control unit and comprising a housing, a plurality of interpoles, and a plurality of short poles, wherein the interpoles are disposed in the housing, a first interval is formed between two adjacent short poles, and a second interval equal to the first interval is formed between each interpole and the adjacent short pole, and the magnetic field generating unit generates a navigation signal according to the first control signal so as to control the magnetic element to move in at least one direction within a target region.

2. The apparatus according to claim 1, wherein the magnetic element comprises a magnetic particle, a magnetic drug, a medical catheter, a medical machine, or their combinations.

3. The apparatus according to claim 1, wherein the navigation signal is a magnetic signal for moving the magnetic element by attraction or repulsion.

4. The apparatus according to claim 1, wherein the housing comprises an annular section and an inner side, and the interpoles of the magnetic field generating unit are disposed on the inner side in the housing and have same intervals arranged around an inner periphery of the annular section.

5. The apparatus according to claim 4, wherein when the number of the interpoles is equal to three, an included angle between the interpoles at a center point of the annular section in the housing is equal to 120 degrees.

6. The apparatus according to claim 4, wherein an included angle between the adjacent short poles at a center point of the annular section in the housing is equal to 5, 10, 12 or 15 degrees.

7. The apparatus according to claim 1, wherein the housing is a substantially hollow cylinder.

8. The apparatus according to claim 1, wherein the housing and at least one of the interpoles and the short poles are integrally formed.

9. The apparatus according to claim 1, wherein the number of the interpoles in the magnetic field generating unit is three or more.

10. The apparatus according to claim 1, wherein the number of the short poles in the magnetic field generating unit is equal to 69, 33, 27 or 21.

11. The apparatus according to claim 1, wherein the magnetic field generating unit further comprises a plurality of windings respectively disposed corresponding to the interpoles.

12. The apparatus according to claim 11, wherein each of the windings has a plurality of coils located between the interpoles and the short poles.

13. The apparatus according to claim 1, further comprising: a moving unit electrically connected with the control unit for moving the magnetic element relative to the moving unit in an additional direction to the target region according to the second control signal.

14. The apparatus according to claim 13, wherein the moving unit comprises a patient table and a driver, and the driver drives the patient table to move in the additional direction according to the second control signal, so that the magnetic element is moved relative to the moving unit to the target region.

15. The apparatus according to claim 1, wherein the first control signal comprises a direct current signal or a pulse signal.

16. The apparatus according to claim 1, wherein the first control signal comprises an over drive current portion.

17. The apparatus according to claim 16, wherein the overdrive current portion of the first control signal is in phase or out of phase.

* * * * *